United States Patent
Wiener et al.

(12) 
(10) Patent No.: US 6,342,390 B1
(45) Date of Patent: *Jan. 29, 2002

(54) LIPID VESICLES CONTAINING ADENO-ASSOCIATED VIRUS REP PROTEIN FOR TRANSGENE INTEGRATION AND GENE THERAPY

(75) Inventors: Stephen M. Wiener, Bethesda; John A. Chiorini; Brian Safer, both of Silver Spring; Robert M. Kotin, Rockville, all of MD (US); Matthew D. Weitzman, La Jolla, CA (US); Roland A. Owens, Arlington, VA (US)

(73) Assignee: The United States of America as represented by the Secretary of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/344,729

(22) Filed: Nov. 23, 1994

(51) Int. Cl.$^7$ ............................................. C12N 15/00
(52) U.S. Cl. ................ 435/325; 435/320.1; 435/372.3; 435/455; 435/458; 514/2; 514/44; 424/93.1; 424/93.21; 530/350
(58) Field of Search ........................ 435/320.1, 172.3, 435/240.1, 240.2, 240.25, 455, 458, 325–372.3; 424/93.1, 93.21; 514/44, 2; 530/350

(56) References Cited

U.S. PATENT DOCUMENTS

| | | | | |
|---|---|---|---|---|
| 5,139,941 A | * | 8/1992 | Muzyczka et al. | 435/455 |
| 5,354,678 A | | 10/1994 | Lebkowski et al. | 435/455 |
| 5,436,146 A | * | 7/1995 | Shenk et al. | 435/172.3 |
| 5,474,935 A | * | 12/1995 | Chatterjee et al. | 435/320.1 |
| 5,587,308 A | * | 12/1996 | Carter et al. | 435/371 |
| 5,658,785 A | * | 8/1997 | Johnson | 435/367 |
| 5,861,314 A | * | 1/1999 | Philip et al. | 435/372.3 |

FOREIGN PATENT DOCUMENTS

| | | | |
|---|---|---|---|
| WO | 9324641 | * | 12/1993 |
| WO | WO 94/28157 | | 12/1994 |
| WO | 9507995 | * | 3/1995 |
| WO | WO 95/13365 | | 5/1995 |
| WO | WO 95/13392 | | 5/1995 |
| WO | WO 95/14771 | | 6/1995 |

OTHER PUBLICATIONS

Marshall, Science, 269, 1995, 1050–1055.*
Kotin, Hum. Gene Ther., 5, 1994, 793–801.*
Xiao et al., Adv. Drug. Del. Reviews, 12, 1994, 201–215.*
Page et al., J. Cell. Biochem., 18A, 1994, 228.*
Nahreini et al., Gene, 119, 1992, 265–272.*
Weitzman et al., PNAS, 91, 1994, 5808–5812.*
Srivastava et al., PNAS, 86, 1989, 8078–8082.*
Chiorini et al., J. Virology, 68, 1994, 797–804.*
Philip et al., Mol. and Cell. Biol., 14(4), 1994, 2411–2418.*
Kotin et al., EMBO J., 11(13), p. 5071–5078, 1992.*
Hermonat et al., Proc. Nat. Acad. Sci, 81:6466–6470, 1984.*
McLaughlin, et al., J. Virology, 62(6):1963–1973, 1988.*
Wang et al., J. Virology, vol. 68, No. 8, pp. 4847–4856, 1994.*
Im, et al., *Cell*, vol. 61, pp. 447–457 (May 4, 1990).
Ghosh, et al., "Targeting of Liposomes to Hepatocytes" in *Liver Disease*, Wu, et al., eds, Marcel Dekker, Inc., New York, pp. 97–103 (1991).
Snyder, et al., *J. Virol.*, vol. 67, No. 10, pp. 6096–6104 (Oct. 1993).
Chiorini, et al., *J. Virol.*, vol. 68, No. 2, pp. 797–804 (Feb. 1994).
Philip, et al., *Mol. Cell. Biol.*, vol. 14, No. 4, pp. 2411–2418 (Apr. 1994).
Chiorini, et al., *J. Virol.*, vol. 68, No. 11, pp. 7448–7457 (Nov. 1994).

* cited by examiner

*Primary Examiner*—Dave T. Nguyen
(74) *Attorney, Agent, or Firm*—Leydig, Voit, & Mayer, Ltd.

(57) ABSTRACT

A composition for delivering at least one DNA sequence encoding a desired protein or polypeptide (such as a therapeutic agent) to a cell. The composition comprises an adeno-associated virus rep protein (or a nucleic acid sequence encoding an adeno-associated virus rep protein) and a genetic construct including at least one DNA sequence encoding a protein or polypeptide or genetic transcript of interest and a promoter controlling the at least one DNA sequence. The genetic construct also includes a first adeno-associated virus ITR or protein or derivative thereof and a second adeno-associated virus ITR or a portion or derivative thereof. The first and second adeno-associated virus ITRs or portions or derivatives thereof flank the at least one DNA sequence encoding the protein or polypeptide or genetic transcript of interest and the promoter controlling the at least one DNA sequence encoding the protein or polypeptide or genetic transcript of interest. Such a composition provides for integration of genetic material at a specific locus in the human chromosome, while minimizing the possibility of inadvertent inactivation of host genes and minimizing the possibility of viral contamination.

18 Claims, 13 Drawing Sheets

EcoRV between nlacZ and RSV promoter

Polylinker sequence:

malE......GGA AGG ATT TCA GAA TTC GGA TCC TCT AGA GTC GAC CTG CAG GCA AGC TTG....lacz-alpha
            Xmn I        Eco RI  BamHI   Xba I   Sal I   Pst I    Hind III pAAVRSVF9 pCMVMBPRep78 pAAVRSVApoF8

LIPID VESICLES CONTAINING ADENO-ASSOCIATED VIRUS REP PROTEIN FOR TRANSGENE INTEGRATION AND GENE THERAPY

This invention relates to gene transfer wherein a desired gene is delivered to a eukaryotic cell with applications for gene therapy. Such gene delivery may be accomplished in vivo, or may be accomplished in vitro, followed by the in vivo administration of such eukaryotic cells to a host. More particularly, this invention relates to liposomes and similar transfection vehicles which include an adeno-associated virus rep protein, adeno-associated virus ITRs, and DNA encoding a desired protein, polypeptide or genetic transcript, such as messenger RNA, antisense RNA, or a ribozyme.

BACKGROUND OF THE INVENTION

Adeno-associated virus (or AAV) has the unique ability to target the integration of its DNA into a host cell genome in a non-random, locus-specific manner. This is in contrast to other viruses such as retroviruses which integrate at random positions in the host genome.

The left open reading frame of adeno-associated virus encodes the rep proteins. Two promoters located at map positions 5 and 19 (promoters p5 and p19, respectively) control expression of the four proteins derived from this ORF. Rep proteins Rep 78 and Rep 68 are produced from p5 promoted transcripts, and rep proteins Rep 52 and Rep 40 are produced from p19 promoted transcripts. It has been demonstrated in vitro that the p5 promoted rep proteins (rep 78 and Rep 68) bind to a defined region of human chromosome 19 at the integration locus for AAV provirus.

It is therefore an object of the present invention to employ AAV rep protein and the AAV ITRs as part of a gene delivery system for achieving targeted integration of foreign genes. Such targeted integration would provide a more effective and safer method of gene delivery. Other gene delivery techniques achieve low levels of integration, often require actively cycling cells as targets, and if integration occurs, it happens at random sites in the genome. Random integration poses the potential danger of inadvertent activation of a deleterious gene (such as a protooncogene) or inadvertent inactivation of an essential gene.

Many clinical gene therapy experiments or protocols also employ viral-based gene delivery systems. Such procedures pose the risk of contamination with potentially pathogenic wild-type virus, which is a significant safety concern. Also, these systems may result in significant host immune responses to transfected cells that express viral proteins on their surfaces.

BRIEF DESCRIPTION OF THE FIGURES

The invention now will be described with respect to the figures, wherein.

DETAILED DESCRIPTION OF THE INVENTION

Figure 1:
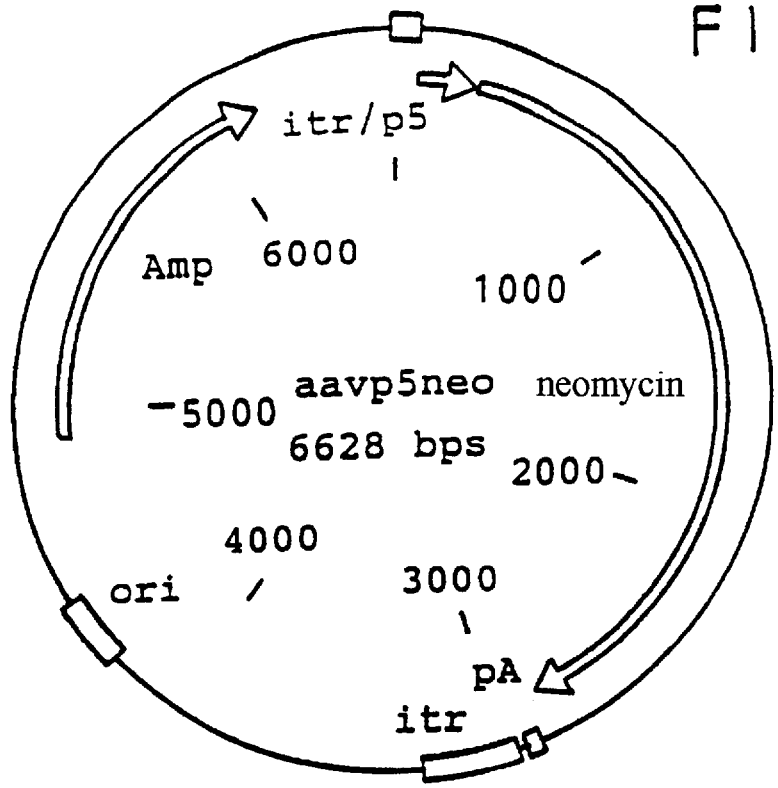
FIG. 1 is a map of plasmid AAVp5neo.

In accordance with an aspect of the present invention, there is provided a composition for delivering a DNA sequence encoding a protein or polypeptide or genetic transcript of interest to a cell. The composition comprises an adeno-associated virus rep protein, or a nucleic acid sequence (DNA or RNA) encoding an adeno-associated virus rep protein. The composition also comprises a genetic construct which includes a DNA sequence encoding a protein or polypeptide or genetic transcript of interest; a promoter controlling the DNA sequence encoding a protein or polypeptide or genetic transcript of interest; a first AAV ITR or portion or derivative thereof; and a second AAV ITR or portion or derivative thereof. The first and second adeno-associated viral ITR's (or portions or derivatives thereof) flank the DNA sequence encoding a protein or polypeptide or genetic transcript of interest and the promoter controlling the DNA sequence encoding the protein or polypeptide or genetic transcript of interest.

In one embodiment, the adeno-associated virus rep protein is selected from the group consisting of Rep 78, Rep 68, Rep 52, Rep 40, and fragments or derivatives thereof. The term "fragments or derivatives thereof" as used herein means that the rep protein may be a protein which has deletion(s) of amino acid residues within the protein structure, and/or may be truncated at the C-terminal and/or the N-terminal, and/or may be mutated such that one or more amino acid residues normally present in the protein structure are replaced with other amino acid residues. Such fragments and derivatives of rep proteins that retain some or all of the same biological activities as the unmodified rep proteins or that may possess modified characteristics.

In one embodiment, the adeno-associated virus rep protein is the Rep 78 protein or a fragment of derivative thereof. In another embodiment, the adeno-associated virus rep protein is the Rep 68 protein or a fragment or derivative thereof.

The adeno-associated virus rep protein may be produced by techniques disclosed in co-pending application Ser. No. 08/067,236, abandoned. For example, the rep protein may be synthesized on an automated protein synthesizer. Alternatively, the rep protein may be produced by genetic engineering techniques.

When the rep protein is produced by genetic engineering techniques, the rep protein may be produced from cells transfected with an expression vehicle including a nucleic acid sequence which encodes the rep protein. In one embodiment, the expression vehicle includes a first DNA sequence encoding an adeno-associated virus rep protein or a fragment or derivative thereof, and a second DNA sequence encoding a protein or a peptide which is not an adeno-associated virus protein or peptide, whereby expression of said first DNA sequence and said second DNA sequence results in expression of a fusion protein including the adeno-associated virus rep protein or fragment or derivative thereof, and the protein or peptide which is not an adeno-associated virus protein or peptide. The protein or peptide which is not an adeno-associated virus protein or peptide may be a bacterial protein or peptide, or a histidine "tag" of 6 to 10 histidine residues.

In one embodiment, the protein or peptide which is not an adeno-associated virus protein or peptide is a bacterial protein. The bacterial protein may be the E. coli maltose-binding protein, or a fragment or derivative thereof. Maltose-binding protein, or MBP, has a high affinity for maltose and amylose. Fusion proteins which include MBP and rep protein can be isolated from lysates prepared from E. coli by adsorption and elution from an amylose affinity column. Thus, large quantities of AAV rep proteins can be isolated and purified, while such AAV rep proteins retain their biological activities.

In another alternative, the rep protein is provided in an appropriate expression vehicle containing a nucleic acid sequence (DNA or RNA) encoding the rep protein. The expression vehicle may be a plasmid vector including the nucleic acid sequence encoding the rep protein.

The genetic construct, which includes a DNA sequence encoding a protein or polypeptide or genetic transcript of interest, a promoter controlling the DNA sequence encoding a protein or polypeptide or genetic transcript of interest, and AAV ITRs or portions thereof which flank the DNA sequence and the promoter, is constructed such that the orientation of the AAV ITRs and the promoter is such that only the DNA sequence encoding the protein or polypeptide or genetic construct of interest, and not any host genes, will be transcribed.

The AAV ITRs which flank the promoter and the DNA sequence controlled by the promoter may be the complete ITR sequences or portions of the ITR sequences, which provide sufficient AAV ITR sequence to facilitate targeted integration by rep protein. In one embodiment, the genetic construct includes at least the double-stranded oligonucleotides containing the AAV ITR A/A' and D'/D regions, which are sufficient for the rep functions believed to be needed for integration; non-covalent binding, endonuclease action, covalent binding, helicase action, and recruitment of host cell enzymes including DNA polymerases. An essential feature in the A/A' region that facilitates non-covalent binding is the imperfect $[GCTC]_4$ repeat, and oligonucleotides can be constructed with alterations in this imperfect repeat sequence or in adjacent sequences that will effect non-covalent binding and/or nicking and covalent binding. Alterations also may include modifications to the ITR hairpin sequences.

The genetic construct may be part of a plasmid, a fragment excised from a plasmid, a large synthetic oligonucleotide, or a "no-end" AAV DNA (i.e., a continuous strand of DNA joined at each end by the AAV ITRs, resulting in a continuous double-stranded DNA molecule).

In one embodiment, the DNA sequence which encodes a protein or polypeptide of interest encodes a therapeutic agent. The term "therapeutic" is used in a generic sense and includes treating agents, prophylactic agents, and replacement agents.

DNA sequences encoding therapeutic agents which may be placed into the genetic construct include, but are not limited to, DNA sequences encoding tumor necrosis factor (TNF) genes, such as TNF-$\alpha$, interferons, such as Interferon-$\alpha$, Interferon-$\beta$, and Interferon-$\gamma$; genes encoding interleukins such as IL-1, IL-1-B, and Interleukins 2 through 14; gene encoding GM-CSF; genes encoding adenosine deaminase or ADA; genes encoding cellular growth factors or cytokines, such as epithelial growth factor (EGF), keratinocyte growth factor (KGF), and lymphokines, which are growth factors for lymphocytes; gene encoding soluble CD4; Factor VII; Factor IX; T-cell receptors; the LDL receptor, ApoE, ApoC, ApoAI, and other genes involved in cholesterol transport and metabolism; the alpha-1 antitrypsin ($\alpha$1AT) gene, the ornithine transcarbamylase gene, the CFTR gene, the insulin gene, negative selective markers or "suicide" genes, such as viral thymidine kinase genes, such as the Herpes Simplex Virus thymidine kinase gene, the cytomegalovirus thymidine kinase gene, and the varicella-zoster virus thymidine kinase gene; superoxide dismutase genes, such as Cu-SOD, Mn-SOD, and Zn-SOD; Fc receptors for antigen-binding domains of antibodies, and antisense sequences which inhibit viral replication, such as antisense sequences which inhibit replication of hepatitis B or hepatitis non-A non-B virus. Additional therapeutic agents include genetic transcripts such as a messenger RNA, antisense RNA, or ribozymes. It is to be understood, however, that the scope of the present invention is not intended to be limited to the specific therapeutic agents described hereinabove.

The DNA sequence encoding the therapeutic agent may be the native nucleic acid sequence which encodes the therapeutic agent or a fragment or derivative of the native nucleic acid sequence which encodes a fragment or derivative of the therapeutic agent, which retains the same biological activity of the unmodified therapeutic agent, or an allelic variant thereof. The term "allelic variant" as used herein means that the allelic variant is an alternative form of the native nucleic acid sequence which may have a substitution, deletion, or addition of one or more nucleotides, which does not alter substantially the function of the encoded therapeutic agent. The DNA sequence may encode the full length therapeutic agent or may encode a fragment or derivative of the therapeutic agent, and the DNA sequence may further include a leader sequence or portion thereof, a secretory signal or portion thereof of the gene encoding the therapeutic agent, and/or may further include a trailer sequence or portion thereof of the gene encoding the therapeutic agent.

The DNA sequence encoding the therapeutic agent is under the control of a suitable promoter. Suitable promoters which may be employed include, but are not limited to, adenoviral promoters, such as the adenoviral major late promoter; or heterologous promoters, such as the cytomegalovirus (CMV) promoter; the Rous Sarcoma Virus (RSV) promoter; inducible promoters, such as the MMTV promoter, the metallothionein promoter; heat shock promoters; the albumin promoter; and the ApoAI promoter. Alternatively, the gene may be under the control of its own native promoter. It is to be understood, however, that the scope of the present invention is not to be limited to any specific promoters.

The rep protein or DNA encoding the AAV rep protein and the genetic construct may be administered to a host in vivo or to eukaryotic cells in vitro. In one embodiment, the rep protein is complexed with the genetic construct and the complex of the rep protein and the genetic construct is introduced into eukaryotic cells in vitro via electroporation or an encapsulating medium such as a liposome or an adenovirus capsid. In another embodiment, the AAV rep protein (or an expression vehicle including a nucleic acid sequence encoding AAV rep protein) and the genetic construct are encapsulated within a liposome and administered in vivo to a patient, whereby the rep protein facilitates integration of the genetic construct into a human chromosome at a defined chromosomal locus, Chromosome 19, 13.4-qter. The rep protein or expression vehicle including a nucleic acid sequence encoding rep protein, and the genetic construct may be encapsulated within the liposome or adenovirus capsid by means known to those skilled in the art. The use of a defined chromosome target minimizes the likelihood of inadvertent inactivation of any host genes.

In one embodiment, the composition further includes a ligand which binds to a desired cell type, tissue, or organ, or a ligand which is non-tissue specific. Examples of ligands include, but are not limited to, adenovirus pentons, fiber trimers, or inactivated adenovirions; fusogenic proteins derived from Sendai virus, Semliki forest virus, and influenza fusogenic peptides; asialoglycoprotein, which binds to the asialoglycoprotein receptor of liver cells; membrane bound cytokines; tumor necrosis factors (or TNF's) such as, for example, TNF-alpha and TNF-beta; transferrin, which binds to receptors on liver cells; Interleukin-2 which binds to receptors on activated T-cells, and neural tissue cells; ApoB, which binds to the LDL receptor of liver cells; alpha-2-macroglobulin, which binds to the LRP receptor of liver cells; alpha-1 acid glycoprotein, which binds to the asialoglycoprotein receptor of liver; mannose-containing peptides, which bind to the mannose receptor of macrophages; sialyl-Lewis-X antigen-containing peptides, which bind to the ELAM-1 receptor of activated endothelial cells; CD34 ligand, which binds to the CD34 receptor of hematopoietic progenitor cells; CD40 ligand, which binds to the CD40 receptor of B-lymphocytes; ICAM-1, which binds to the LFA-1 (CD11b/CD18) receptor of lymphocytes, or to the Mac-1 (CD11a/CD18) receptor of macrophages; M-CSF, which binds to the c-fms receptor of spleen and bone marrow macrophages; circumsporozoite protein, which binds to hepatic *Plasmodium falciparum* receptor of liver cells; VLA-4, which binds to the VCAM-1 receptor of activated endothelial cells; LFA-1, which binds to the ICAM-1 receptor of activated endothelial cells; NGF, which binds to the NGF receptor of neural cells; HIV gp120 and Class II MHC antigen, which bind to the CD4 receptor of T-helper cells; the LDL receptor binding region of the apolipoprotein E (ApoE) molecule; colony stimulating factor, or CSF, which binds to the CSF receptor; insulin-like growth factors, such as IGF-I and IGF-II, which bind to the IGF-I and IGF-II receptors, respectively; Interleukins 1 through 14, which bind to the Interleukin 1 through 14 receptors, respectively; and the Fc antigen-binding domain of an immunoglobulin. The ligand may be conjugated to the rep protein or conjugated to a complex of rep protein and the genetic construct or, when a liposome is employed to deliver the rep protein and genetic construct, the ligand may be anchored in the phospholipid bilayer of the liposome.

The DNA sequence encoding the therapeutic agent is administered in an amount effective to produce a therapeutic effect in a host. The host may be an animal host, and in particular a mammalian host. The mammalian host may be a human or non-human primate. The exact dosage of DNA to be administered is dependent upon various factors, including the age, weight, and sex of the patient, the type of genetic construct employed, the nature of the disorder to be treated, the type of AAV rep protein employed, the formulation of the lipid vesicle employed to deliver the DNA, and the type of cells to be transfected with the DNA.

In another embodiment, the composition of the present invention may be employed in an animal model, wherein the composition of the present invention is administered to an animal in vivo. The animal is then evaluated for expression of the therapeutic agent in vivo in order to determine the effectiveness of a possible gene therapy treatment in a human patient.

Alternatively, the composition of the present invention, which includes a DNA sequence encoding a protein or polypeptide or genetic transcript of interest, may be administered to eukaryotic cells, such as human cells, in vitro, whereby the cells are transfected with the genetic construct including the DNA sequence encoding the protein or polypeptide or genetic transcript of interest. In such an embodiment, the genetic construct may be administered in an amount of from about 0.75 $\mu$g to about 1.5 $\mu$g of DNA per $5 \times 10^5$ cells, preferably at about 1.25 $\mu$g of DNA per $5 \times 10^5$ cells. The eukaryotic cells then may be administered to a host as part of a gene therapy procedure, whereby such eukaryotic cells express the protein or polypeptide or genetic transcript of interest in a host.

In another alternative, the composition of the present invention may be employed to transfect eukaryotic cells in vitro, whereby such transfected eukaryotic cells are cultured in order to produce a desired protein or polypeptide of interest in vitro.

EXAMPLES

The invention now will be described with respect to the following examples; however, the scope of the present invention is not intended to be limited thereby.

Example 1

A. Construction of pAAVRnLacZ

Figure 2:
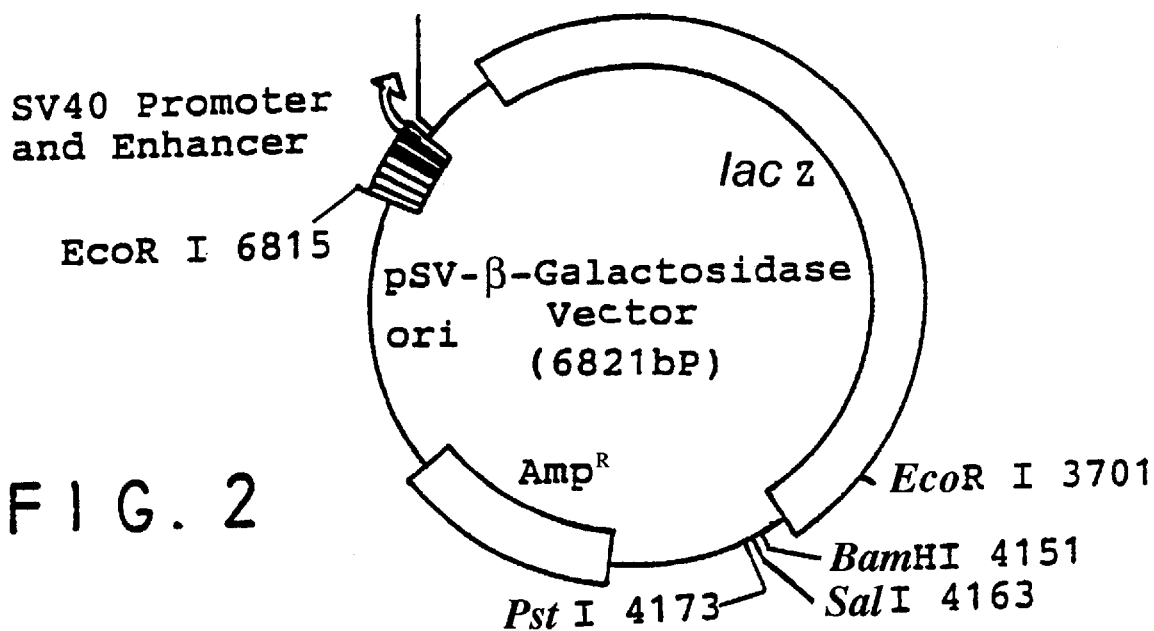
FIG. 2 is a map of plasmid pSv-β-galactosidase.
Figure 3:
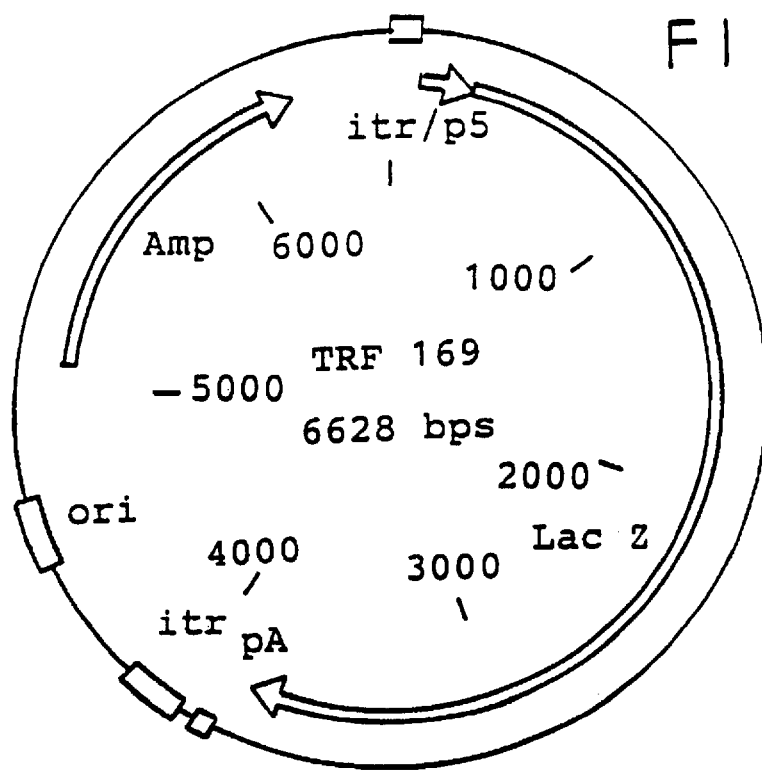
FIG. 3 is a map of plasmid TRF169.

Plasmid AAVp5neo (Flotte, et al. , *Am. J. Respir. Cell Mol. Biol.,* Vol. 7, pgs. 349–356 (1992)) (FIG. 1) was cut with HindIII and KpnI to remove the neo$^R$ gene, and the KpnI/BamHI fragment from pSV-βgalactosidase (Promega) (FIG. 2) was blunted and cloned into the blunted sites of the plasmid to form plasmid TRF169. (FIG. 3).

Figure 4:
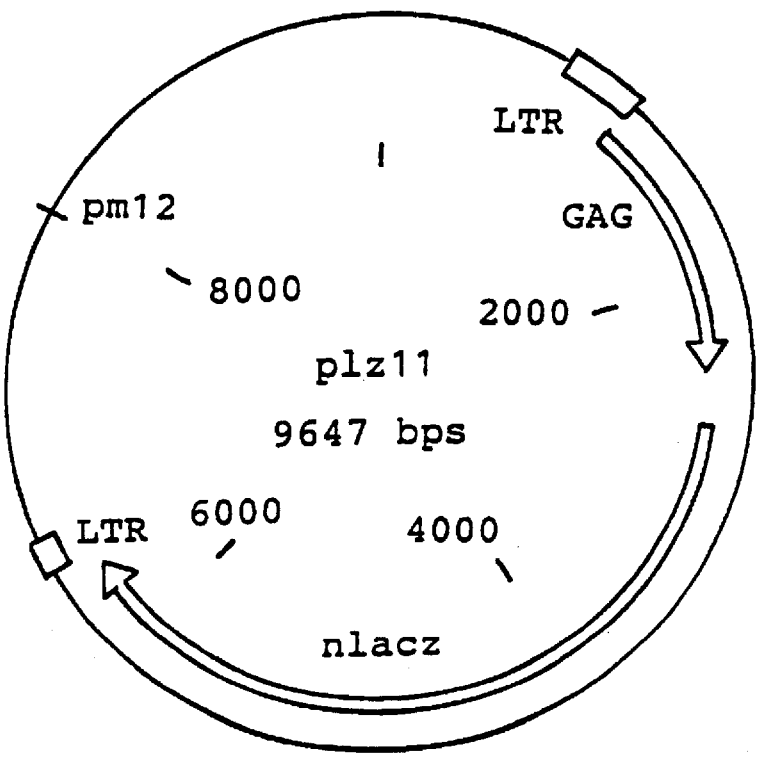
FIG. 4 is a map of plasmid pLZ11.
Figure 5:
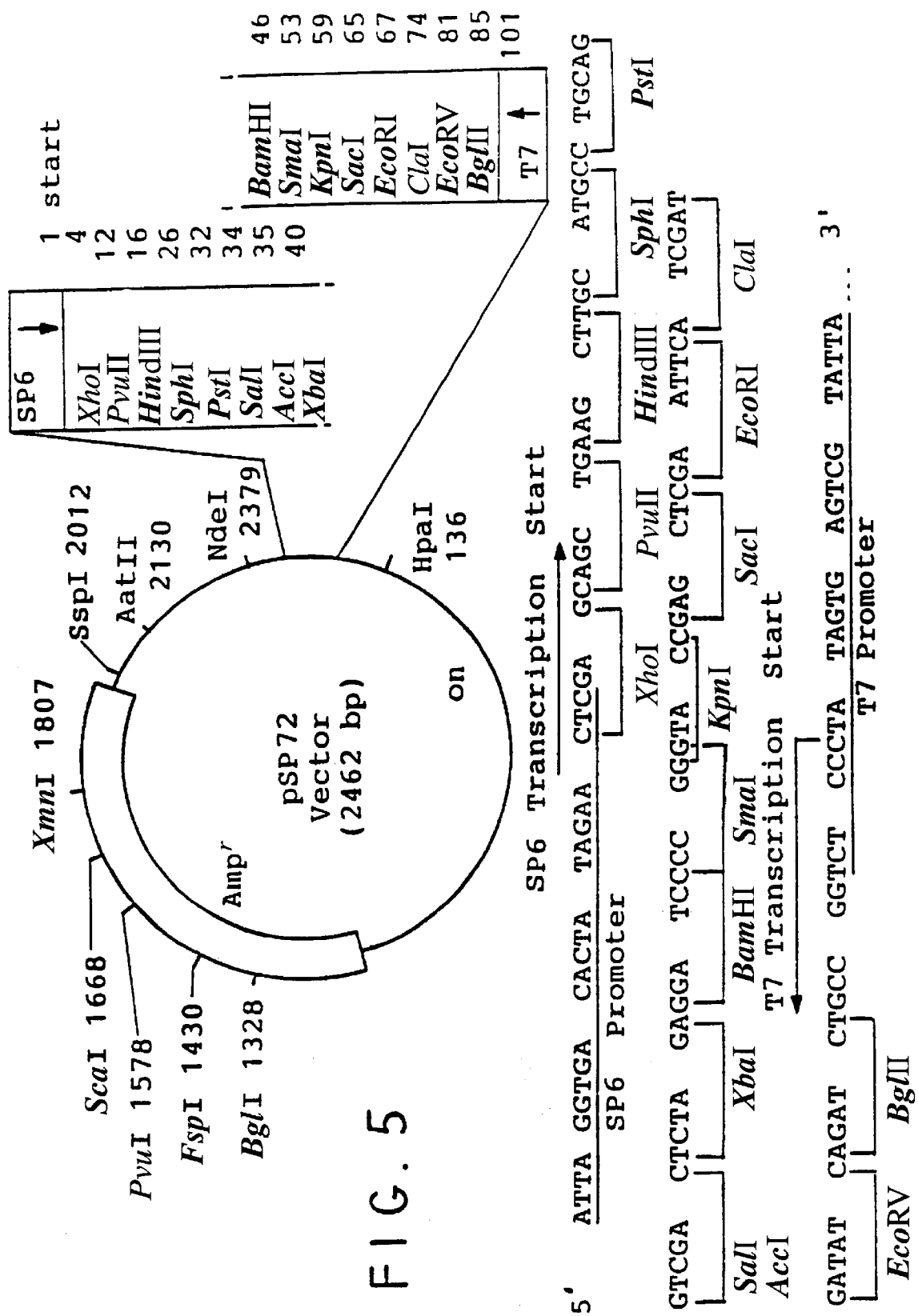
FIG. 5 is a map of plasmid pSP72.
Figure 6:
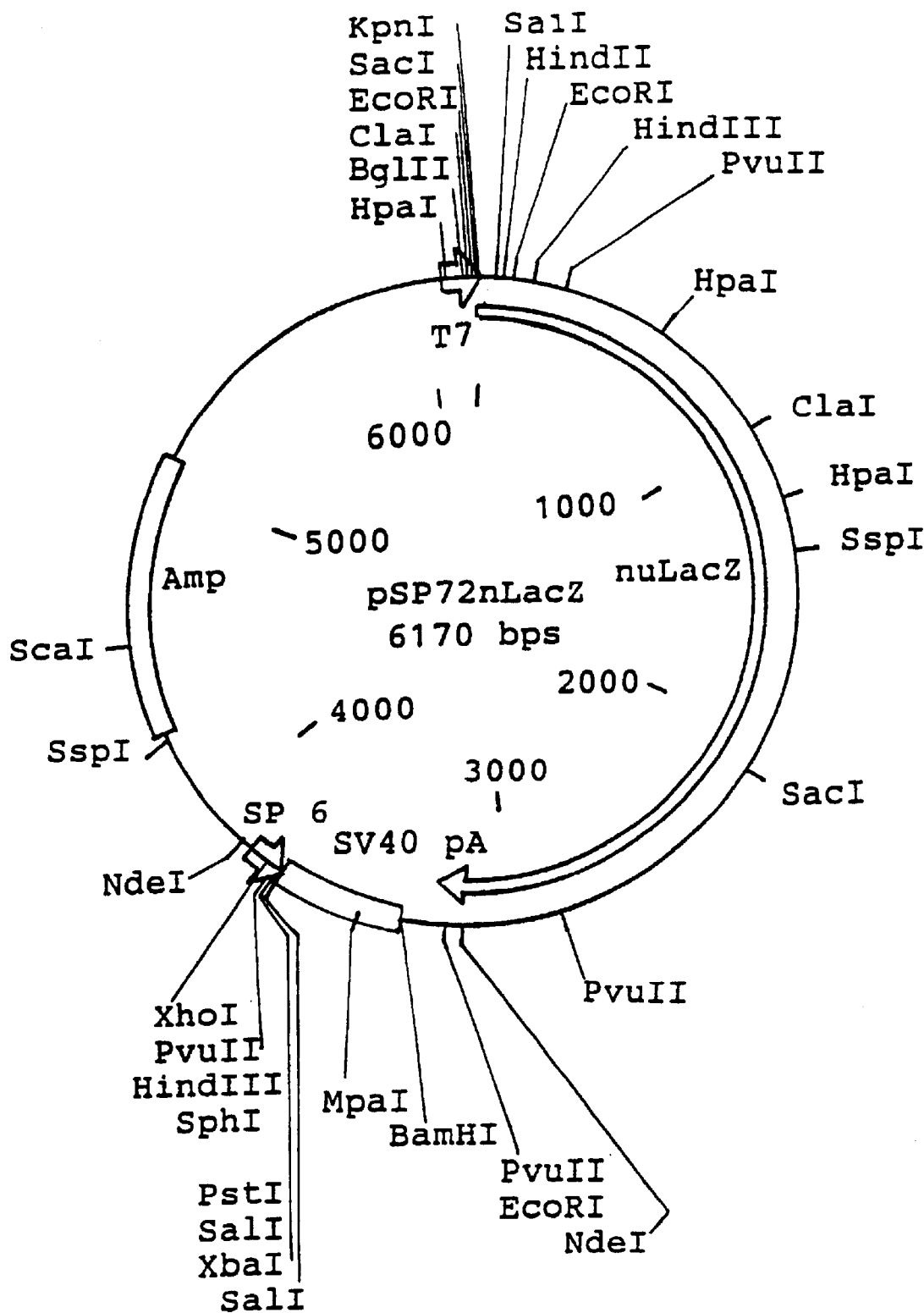
FIG. 6 is a map of plasmid pSP72nlacZ.
Figure 7:
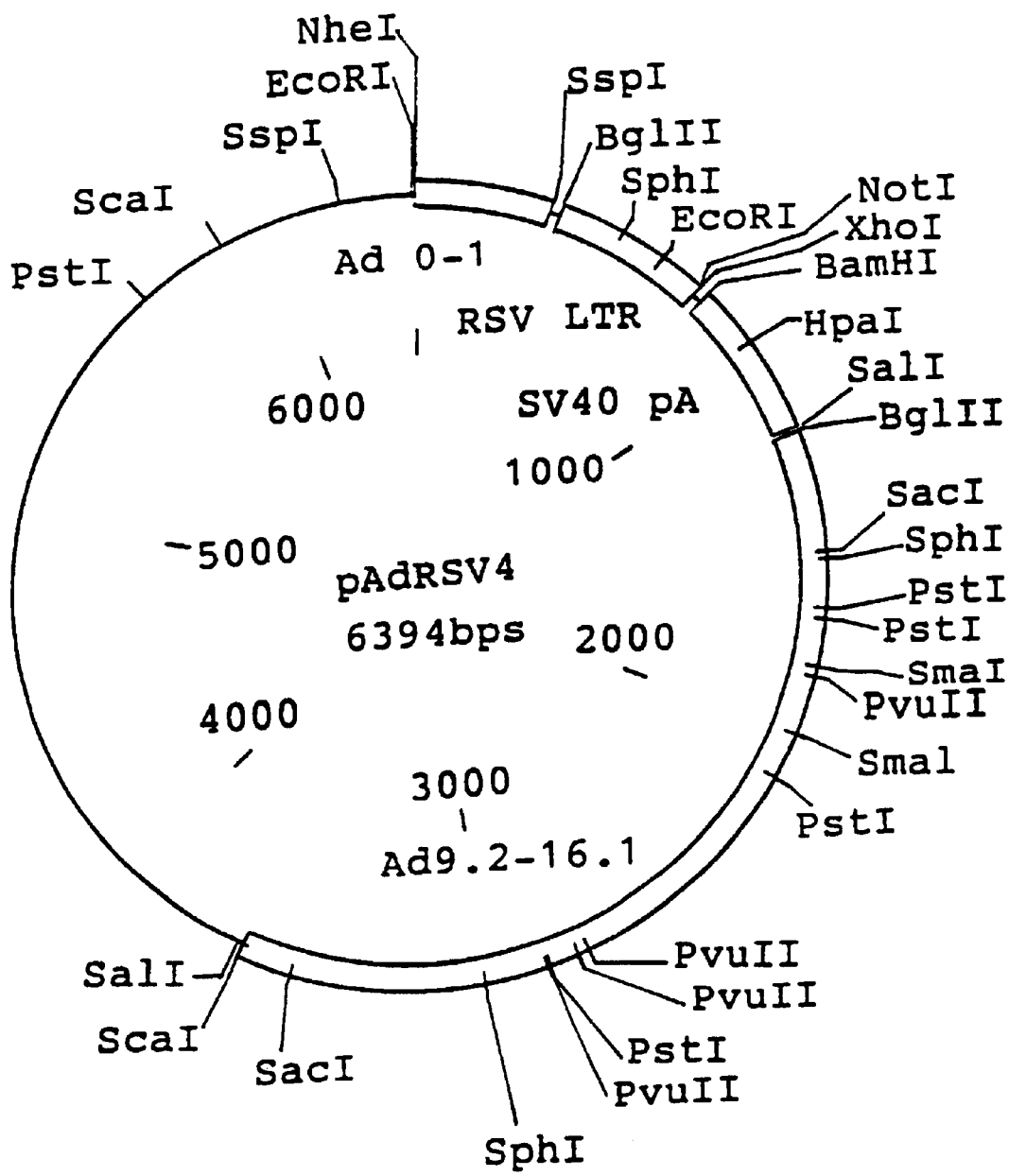
FIG. 7 is a map of plasmid pAdRSV4.
Figure 8:
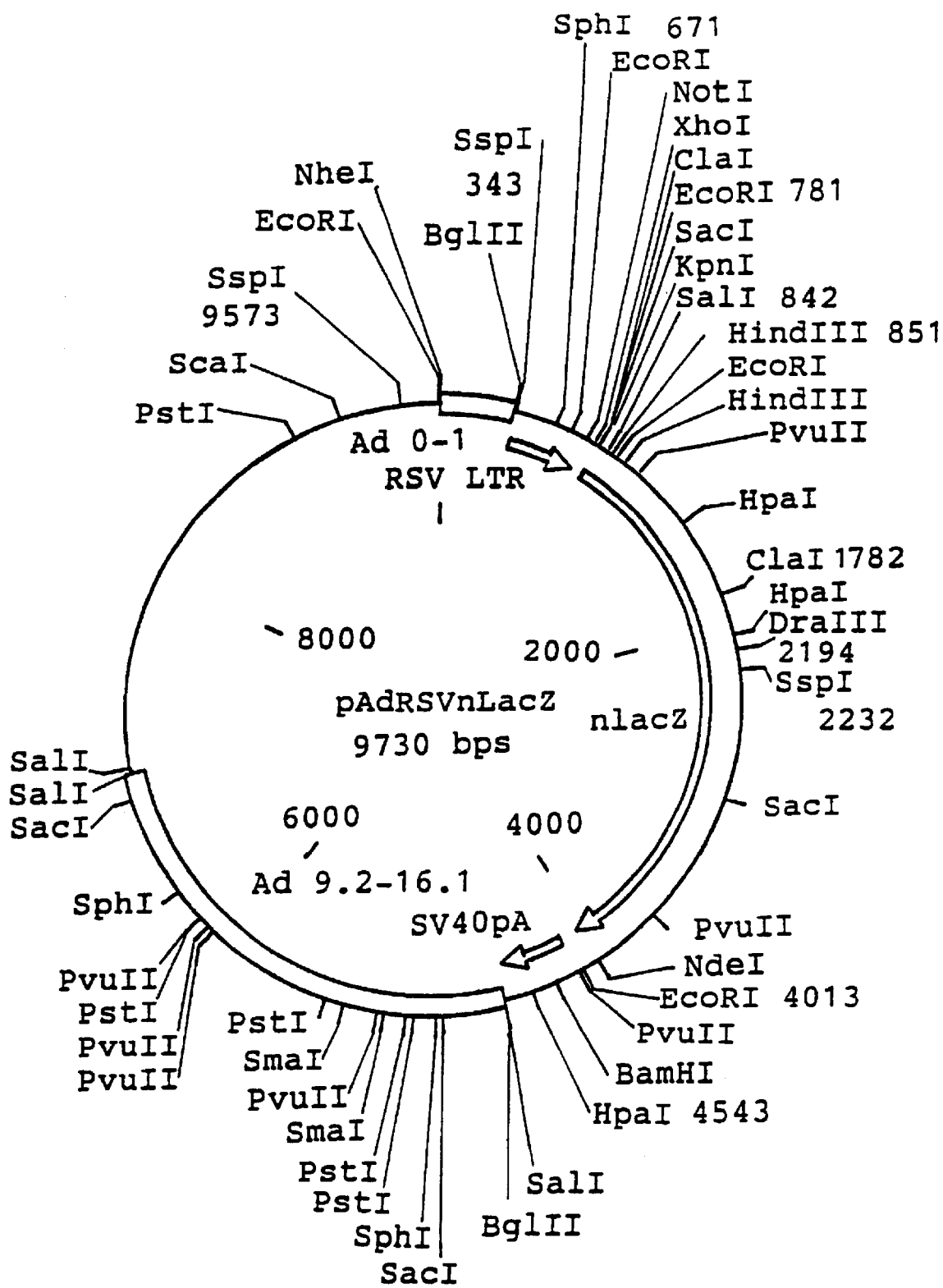
FIG. 8 is a map of plasmid pAdRSVnlacZ.
Figure 9:
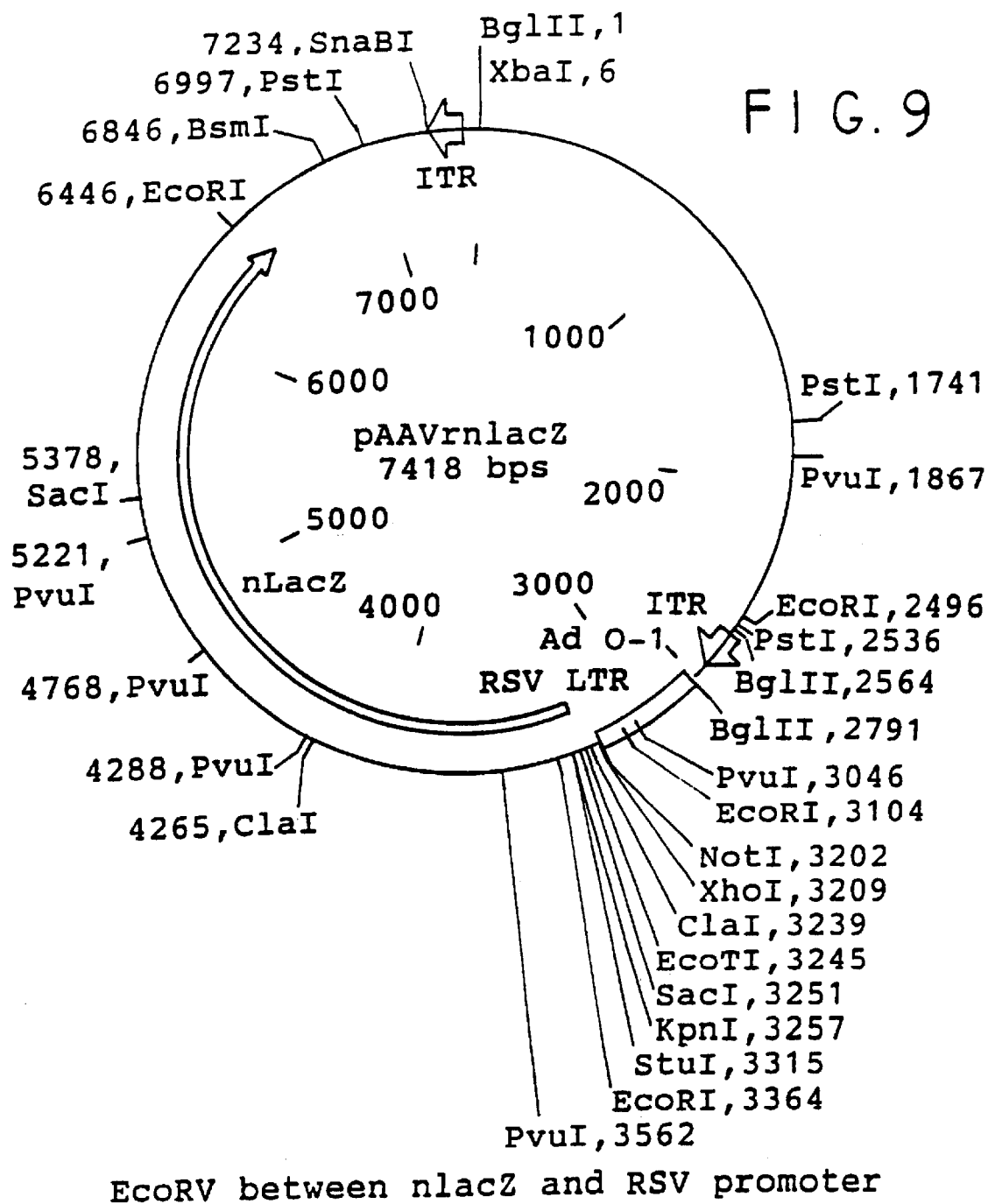
FIG. 9 is a map of plasmid pAAVrnlacZ.

A second plasmid which provided the RSV-LTR promoter and nuclear targeting sequence for the lacZ gene was constructed as follows. The BglII/XbaI fragment containing the nlacZ gene from plasmid LZ11 (Galileo, et al., *Proc. Natl. Acad. Sci.,* Vol. 87, pgs. 458–462 (1990)) (FIG. 4) was cloned into the blunted SmaI and BamHI sites of pSP72 (Promega) (FIG. 5) to form pSP72nLacZ (FIG. 6). From pSP72nlacZ, the BglII/BamHI fragment containing the nlacZ gene was removed and cloned into the BamHI site of adRSV4 (FIG. 7) which was obtained from Dr. Beverly Davidson of the University of Michigan. The resulting plasmid is referred to as pAdRSVnLacZ (FIG. 8).

pAAVrnLacZ (FIG. 9, ATCC No. 69492) was produced by inserting the SspI/DraIII fragment from pAdRSVnLacZ which contained the RSV-LTR promoter, nuclear targeting signal linked to the lacZ gene into the Pm1I/DraIII site of TRF169.

B. Preparation of AAV Rep Proteins (i) Cloning of MBP-Rep 68Δ and MBP-Rep 78

Figure 10:
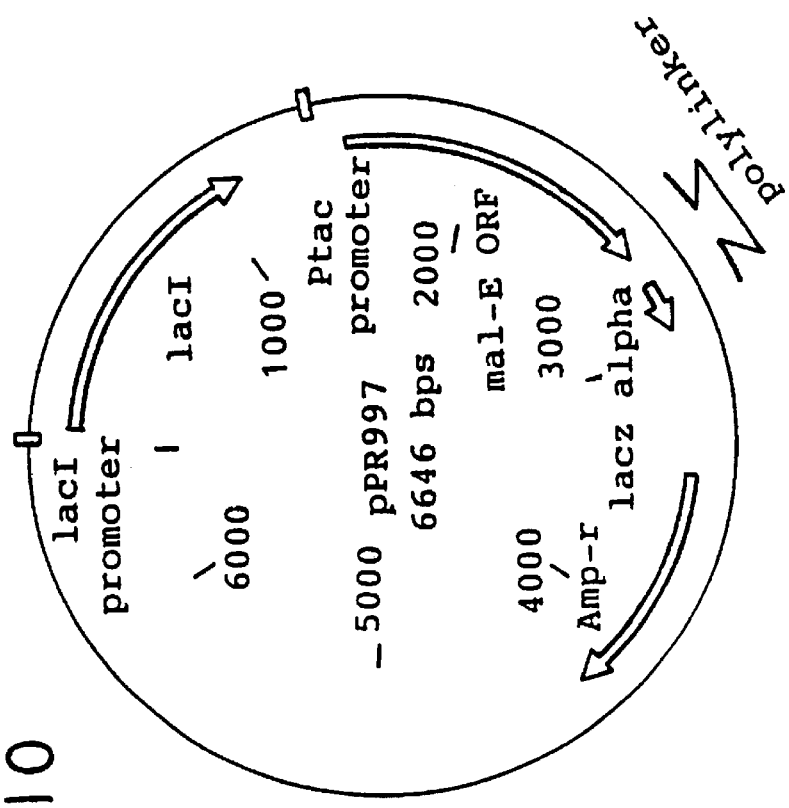
FIG. 10 is a map of plasmid pPR997.
Figure 11:
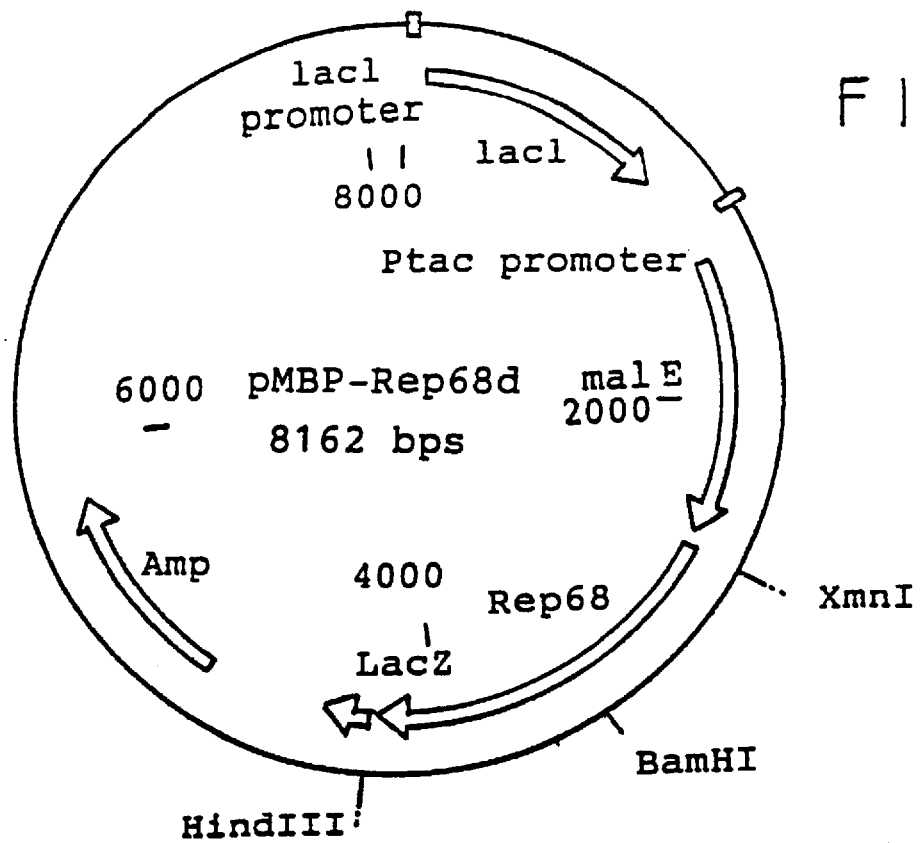
FIG. 11 is a map of plasmid pMBP-Rep 68Δ.

The open reading frames of rep proteins Rep 68 and Rep 78 were generated by PCR amplification. A common 5' primer corresponding to nucleotides 327–346 of adeno-associated virus (codons 3–9 of Rep 68 and the Rep 78 open reading frame) was synthesized and used for both Rep 68 and Rep 78. Initially, Rep 68 was amplified using a 3' primer corresponding to a reverse complement of AAV nucleotides 2029–2048 (codons 570–576). PCR amplification was performed using cloned Pfu polymerase (Stratagene) with buffer. The PCR product was digested with HindIII, which cleaves AAV at nucleotide 1882, and ligated into plasmid pPR997 (FIG. 10) (New England Biolabs), which was digested with XmnI and HindIII. Thus, a Rep 68 gene was inserted into pPR997 in which 16 codons at the 3' terminus were deleted, thus resulting in the formation of a modified Rep 68 protein, sometimes hereinafter referred to as Rep 68Δ, in which the last 16 amino acids at the C-terminal have been deleted. pPR997 includes an *E. coli* malE gene, in which nucleotides 2–26 of the malE gene were deleted, controlled by the *E. coli* tac promoter which includes an operator site for the lacI repressor. pPR997 also includes a polylinker or multiple cloning site. This cloning strategy resulted in the open reading frame of the Rep 68 gene ligating in frame with the malE open reading frame of pPR997 at the 5' end of the Rep 68 gene. The 3'terminus of the Rep 68 gene is a frame-shifted fusion between the AAV Rep 68 open reading frame and the lacZα gene, resulting in an additional 50 residues at the carboxy-terminus. The resulting plasmid is pMBP-Rep 68Δ. (FIG. 11)

Figure 12:
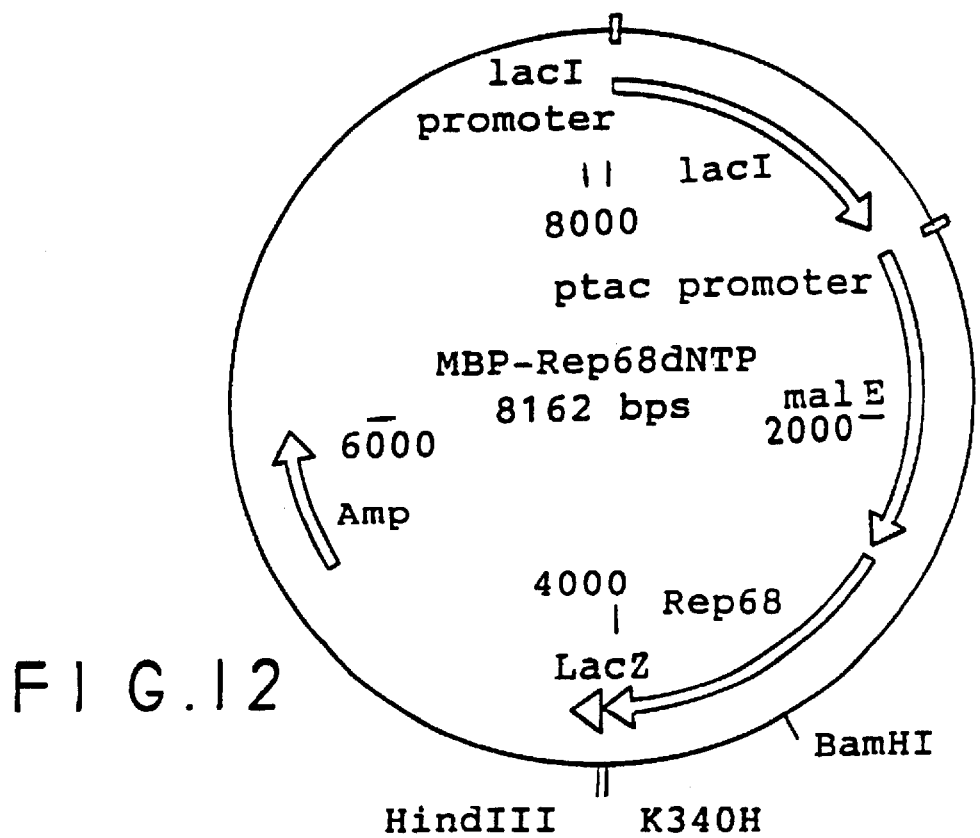
FIG. 12 is a map of plasmid pMBP-Rep 68ΔNTP
Figure 13:
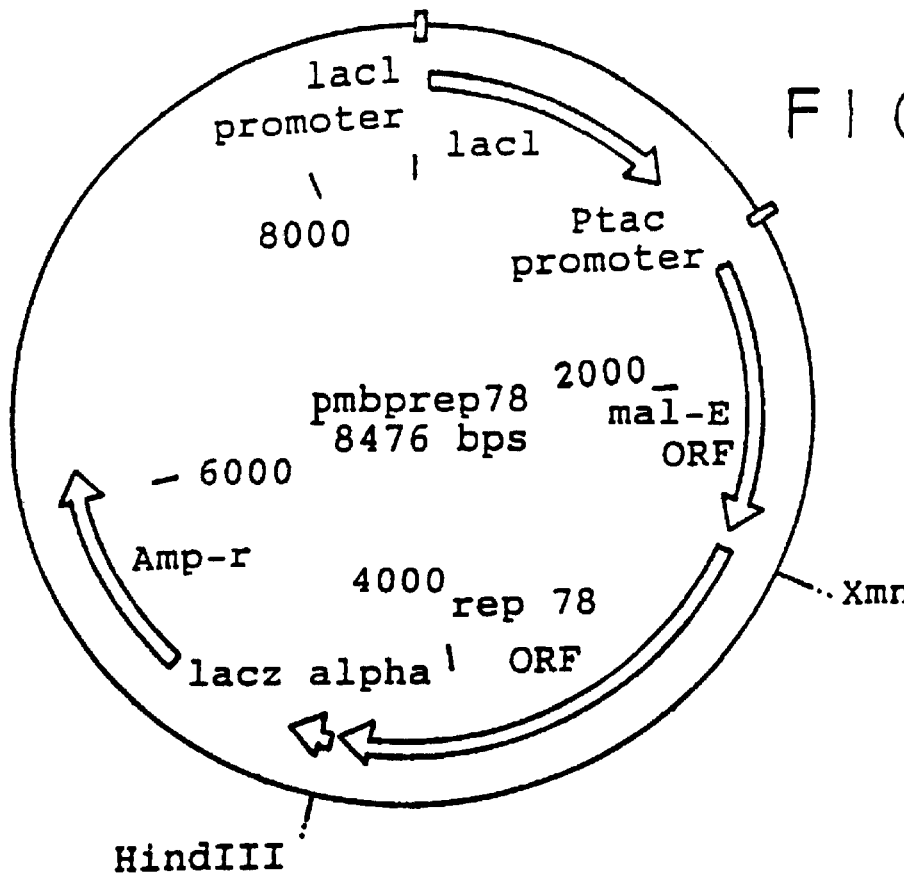
FIG. 13 is a map of plasmid pMBP-Rep 78.

A mutant MBP-Rep 68Δ with a mutation in the putative nucleoside triphosphate (NTP)-binding site was produced by substitution of a BamHI-HindIII fragment from the pHIV rep NTP plasmid with a lysine-to-histidine mutation in codon 340 (K340H) (Owens, et al., *Virology*, Vol. 184, pgs. 14–22 (1991); Owens, et al., *J. Virol.*, Vol. 67, pgs. 997–1005 (1993)) to form pMBP-Rep 68ΔNTP. (FIG. 12). MBP-Rep 68Δ-NTP retains the DNA binding function of MBP-Rep 68Δ; however, other biochemical properties, such as helicase activity, are ablated.

pMBP-Rep 78 was generated by amplifying AAV nucleotides 1872–2239. This sequence includes an overlapping region of Rep 68 and Rep 78 and the 3' terminus of Rep 78. The 5' primer corresponds to AAV nucleotides 1872–1894 and the 3' primer corresponds to the reverse complement of AAV nucleotides 2215–2239, and also incorporates HindIII and XbaI sites. The PCR product was digested with HindIII and ligated into HindIII digested pMBP-Rep 68Δ. The resulting plasmid is pMBP-Rep 78. (FIG. 13)

The MBP-Rep 78 protein is an in-frame fusion protein between the malE open reading frame and the adeno-associated virus open reading frame beginning at codon 3 of the Rep 78 gene. The 3'-terminus utilizes the naturally occurring stop codon of the rep gene, and therefore there are no non-viral carboxy terminus residues.

(ii) Protein Expression

*E. coli* organisms were transfected with pMBP-Rep 68Δ NTP or pMBP-Rep 78 according to standard techniques. The DNA encoding MBP-Rep 68Δ NTP or MBP-Rep 78 is under the control of the *E. coli* tac promoter which is repressed by the lacI repressor gene product. Addition of IPTG prevents binding of the lac repressor to the tac promoter, thereby enabling high levels of expression of MBP-Rep 68Δ NTP or MBP Rep 78. Recombinants that were positive for the correct insert and orientation were screened for expression of fusion protein. The bacterial clones that produced a protein of the predicted molecular weight were grown on a larger scale.

One liter cultures of bacteria transformed with pMBP-Rep 68Δ NTP or pMBP-Rep 78 were obtained. A bacterial pellet was obtained from each culture by centrifugation, and each bacterial pellet was resuspended in 0.05 vol. of column buffer (200 mM NaCl, 20 mM Tris-Cl (pH 7.4), 1 mM EDTA, and 1 mM dithiothreitol). The bacteria were lysed by sonication by four 30 second pulses. The suspension was cleared by centrifugation at 9,000×g for 20 min. at 4° C.

The supernatant was loaded onto a column packed with amylose-Sepharose resin equilibrated in column buffer. The column then was washed with 10 column volumes of column buffer. The proteins then were eluted with 1×column buffer containing 10 mM maltose. Approximately 1 ml fractions were collected and 2 μl aliquots were analyzed by SDS-polyacrylamide gel electrophoresis on an 8% SDS-polyacrylamide gel. The overall yield of MBP-Rep 68Δ NTP or MBP-Rep 78 from a one-liter culture was from 4 to 12 mg of protein.

C. Preparation of Liposomes Containing AAV Rep Protein and pAAVRnLacZ

Liposomes were made by mixing 3 μl of lipid in 25 μl of Optimem (Gibco) with 25 μl of an Optimem solution containing the plasmid pAAVRnLacZ at a concentration of 0.05 μg/μl (yielding 1.25 μg DNA). The Optimem solution containing the plasmid was preincubated for ½ hour at 37° C. with either (i) MBP-Rep 78 in amounts of 0.98 μg, 0.42 μg, 0.26 μg, or 0.19 μg; (ii) MBP-LacZ in amounts of 1.5 μg, 0.15 μg, or 0.015 μg; or (iii) MBP-Rep 68 Delta NTP in amounts of 1.5 μg, 0.15 μg, or 0.015 μg.

D. Transfection of Cells with Liposomes Including AAV Rep Protein and pAAVRnLacZ One-half hour after the solutions were mixed to form liposomes, the solution containing the liposomes was added to human hepatoma derived, Hep G-2 cells that had been washed with PBS and then covered with a minimal volume of Optimem. The liposomes were added in an amount such that 1.25 μg of total plasmid DNA was added per $5 \times 10^5$ cells. Prior to contact of the cells with the liposomes, the cells had been grown in DMEM with 10% fetal calf serum and 2 mM glutamine. The cells were grown in an incubator having a 5% $CO_2$ atmosphere, and at 37° C.

Eighteen hours after the liposomes were added to the cells, serum containing medium was added. Thirty-three hours after liposome addition, the cells were washed with PBS, trypsinized and serum-containing medium was added to stop the trypsin action, and the cells were transported on ice for cell cytometry.

To determine the optimal ratio between rep protein and a 5' labeled AAV ITR, experiments had been conducted using a covalent linkage assay. The assay is dependent on three rep protein functions (non-covalent binding, endonuclease activity, and covalent binding). (Im, et al., *J. Virol.*, Vol. 63, pgs. 3095–3114 (1989); Chiorini, et al., *J. Virol.*, Vol. 68, pgs. 7448–7457 (1994)). Maximal covalent bond formation occurred when the MBP Rep 78/ITR molar ratio was 9:1.

Using this information, cytometry was conducted at 36 hours post-transfection. Cells were counted and viability was determined by trypan blue and propidium iodide staining. Greater than 95% of the cells were viable, which demonstrated that liposomes containing rep protein were not toxic. Cells expressing lacZ were detected by the use of the fluorescent B-galactosidase substrate fluorescein di-Beta galactopyranoside (FDG) and sorted into positive (+) and negative (−) populations. Non-viable cells were excluded from all % (+) determinations and sorting. Cytometry also was done to verify the purity of the sorted populations. This showed the sorted populations to be greater than 99% pure.

The percentage of positive cells (i.e., cells which expressed the lacZ gene) for Hep G-2 cells treated with MBP-Rep 78 is given in Table I below.

TABLE I

| MBP-Rep78/1.25 μg plasmid DNA/5 × $10^5$ cells | | | |
|---|---|---|---|
| μg Rep 78 | picomoles Rep 78 | moles Rep 78/ moles plasmid | % (+) |
| 0.98 | 8.5 | 34 | 49 |
| 0.42 | 3.6 | 14 | 43 |
| 0.26 | 2.3 | 9 | 7 |
| 0.16 | 1.7 | 7 | 11 |
| 0 | 0 | 0 | 1 |

The percentage of positive cells (i.e., cells which expressed the lacZ gene) at 36 hours post-transfection for HepG-2 cells treated with MBP-lacZ is given in Table II below.

TABLE II

MBP-lacZ/1.25 µg plasmid/5 × 10⁵ cells

| µg lacZ | pico moles lacZ | moles lacZ/ moles plasmid | % (+) |
|---|---|---|---|
| 1.5 | 33 | 132:1 | 0 |
| 0.15 | 3.3 | 13:1 | 0 |
| 0.015 | 0.3 | 1:1 | 22 |

The percentage of positive cells which expressed the lacZ gene at 36 hours post-transfection for HepG-2 cells treated with MBP-Rep 68-delta NTP is given in Table III below.

TABLE III

MBP-Rep 68 delta NTP/1.25 µg plasmid DNA/5 × 10⁵ cells

| µg Rep 68-delta NTP | pico moles Rep 68-delta NTP | moles Rep 68-delta NTP/moles plasmid | % (+) |
|---|---|---|---|
| 1.5 | 14 | 56:1 | 0.5 |
| 0.15 | 1.4 | 5.6:1 | 35 |
| 0.015 | 0.14 | 0.56:1 | 35 |

Based on these results, MBP-Rep 78 appeared to cause earlier expression of the lacZ gene in a dose-related fashion. This was a specific rep protein effect, because MBP-lacZ, a protein with no rep protein functions, had the opposite effect, tending to show fewer positive cells with increasing amounts of the protein. The MBP-Rep 78 effect appeared to require rep protein activities other than DNA binding, since MBP-Rep 68 delta NTP, a mutant rep protein able to bind non-covalently but not nick AAV ITRs, had the same effect as MBP-lacZ.

The cells were maintained in culture for approximately 2 months and then sent for repeat cytometric analysis. Cell viability remained high. The cells then were preincubated with chloroquine to reduce any background positivity, and then were stained with fluoroscein-di-Beta galactopyranoside (FDG) as hereinabove described. Non-viable cells were excluded by propidium iodide and cytometry, and the percent positive cells was determined for viable cells.

The percentage of positive cells (i.e., cells which expressed the lacZ gene) at 2 months after transfection among cells that were positive at 36 hours after transfection, and which were treated with MBP-Rep 78, is given in Table IV below.

TABLE IV

MBP-Rep 78/1.25 µg DNA/5 × 10⁵ cells

| µg Rep 78 | µ moles Rep 78/ moles plasmid | % (+) |
|---|---|---|
| 0.98 | 34:1 | 10 |
| 0.42 | 14:1 | 8 |
| 0.26 | 9:1 | 18 |
| 0.19 | 7:1 | 13 |
| 0.00 | 0 | 7 |

The percentage of positive cells at 2 months after transfection among cells that were negative at 36 hours after transfection, and which were treated with MBP-Rep 78, is given in Table V below.

TABLE V

MBP-Rep 78/1.25 µg DNA/5 × 10⁵ cells

| µg Rep 78 | µ moles Rep 78/ mles plasmid | % (+) |
|---|---|---|
| 0.98 | 34:1 | 80 |
| 0.42 | 14:1 | 53 |
| 0.26 | 9:1 | 22 |
| 0.19 | 7:1 | 22 |
| 0 | 0 | 5 |

The results of Tables IV and V indicated a dose-dependent MBP-Rep 78 effect that was greatest with cells which originally had been negative. These cells had a high percentage of FDG-positive cells, and this percentage increased with increasing dosage of Rep 78 employed. The cells which had been positive at 36 hours post-transfection showed a much lower percentage of stable positive cells and while Rep 78 appeared to increase long term percentage of positive cells, there was no dose effect.

These results indicate that MBP-Rep 78, when delivered via a liposome with an ITR-flanked gene, appears to augment, in a dose-dependent fashion, long-term transgene expression in cell culture. Such augmentation of expression is unlikely to have resulted from enhanced integration, as it is unlikely for an extrachromosomal element to persist in culture for two months without continuous positive selection pressure. From the above results, rep protein delivered by liposome appears to have two effects in a cell: (i) enhancement of initial expression of the transgene with a reduced effect on integration (initially positive cells that subsequently had lower levels of persistently positive cells); or (ii) suppression of initial transgene expression while facilitating integration (initially negative cells that subsequently had high levels of long-term positive cells.).

Figure 15:
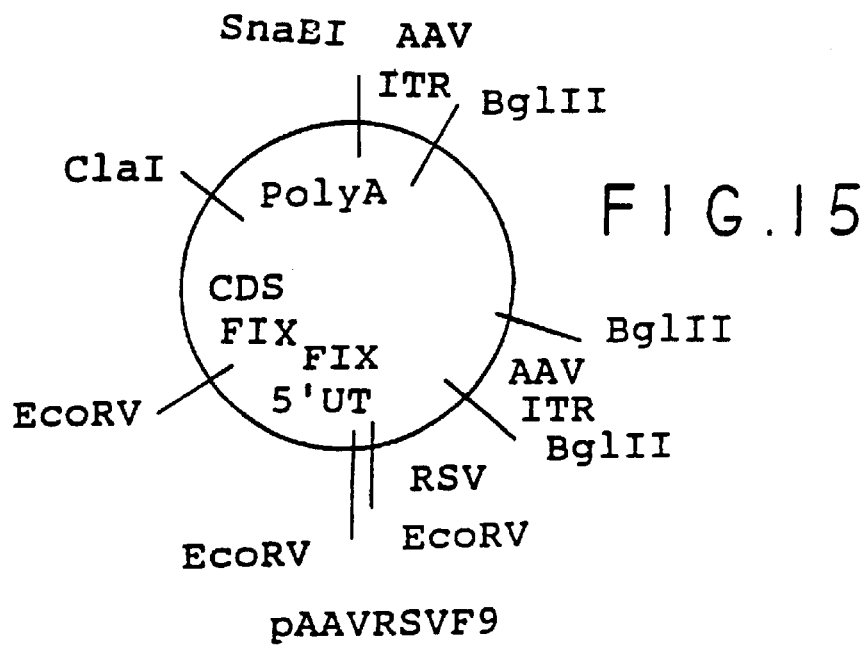
FIG. 15 is a map of plasmid pAAVRSVF9.
Figure 14:
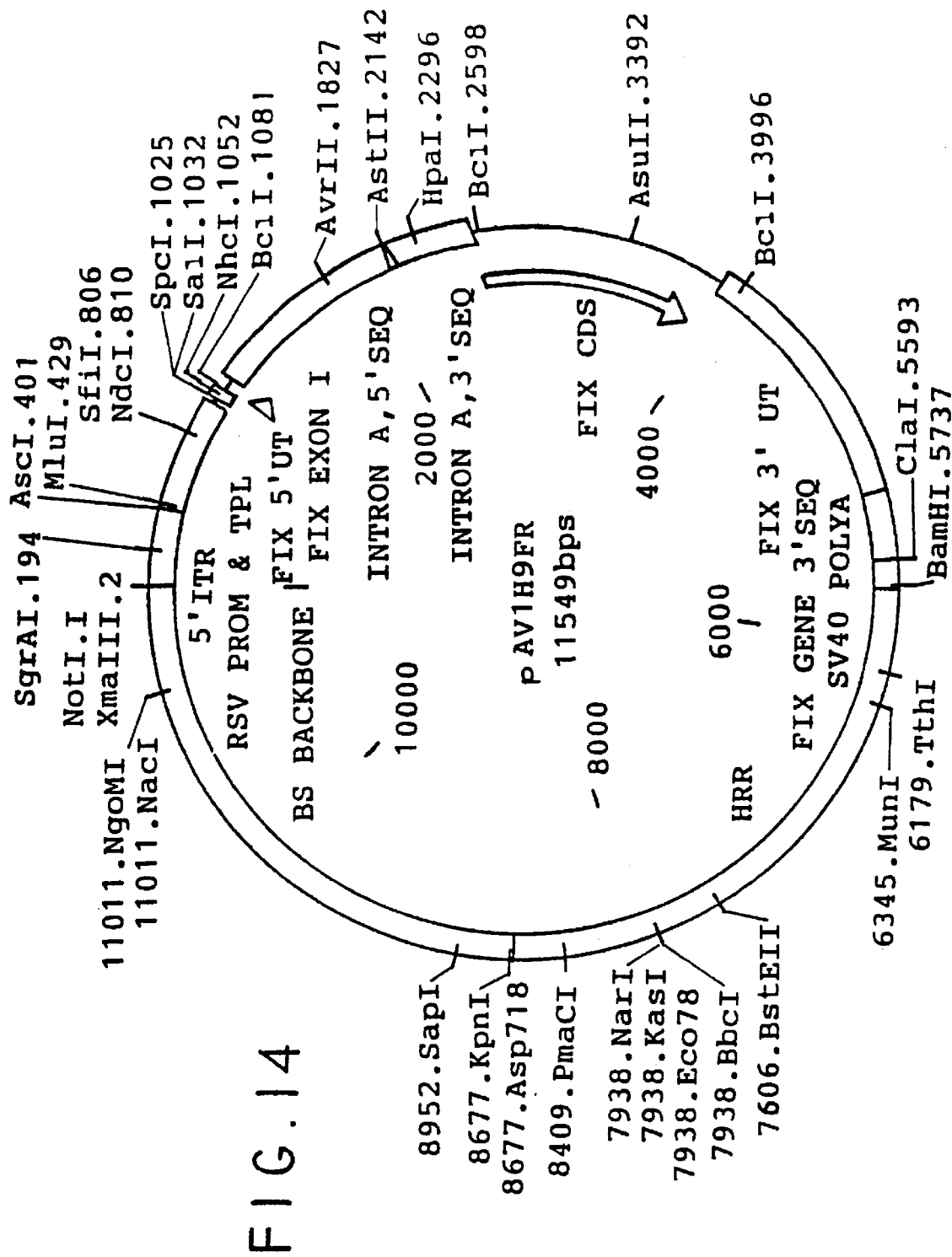
FIG. 14 is a map of plasmid pAv1H9FR.

Example 2
Ex vivo treatment of Hemophilia B Using an AAV Vector for Human Factor IX pAv1H9FR (FIG. 14, which includes an adenovirus 5' ITR, an RSV promoter, a tripartite leader sequence, the 5' untranslated region of the human Factor IX gene, a centrally truncated first intron, the human Factor IX coding region, the 3' untranslated region of the human Factor IX gene, a polyadenylation signal, and an adenovirus homologous recombination region), is digested with SpeI and BamHI to obtain a fragment including the human Factor IX gene and the above-mentioned genomic elements and polyadenylation signal. The fragment is blunt-ended with Klenow, and cloned into the ITR containing fragment of the NotI-BsmI digest of pAAVrnlacZ to obtain pAAVRSVF9. (FIG. 15).

The plasmid pAAVRSVF9 contains the gene for Human Factor IX under the control of the RSV promoter. There are 5' and 3' flanking AAV ITR's:

5'—AAV ITR—RSV Promoter—Human Factor IX gene—Poly A—AAV ITR—3'

A patient with Hemophilia B undergoes a partial hepatectomy using appropriate coagulation factor support. The removed cells are placed into culture at 37° C. One day later the cells are gently washed with IX PBS followed by gentle rewashing with Optimem (Gibco). The cells are covered with a thin layer of Optimem. DNA containing liposomes are added, such that there is a ratio of 1.25 micrograms of DNA added per 5×10⁵ cells.

The liposomes are formed by mixing 3 microliters of lipid in 25 microliters of Optimem (Gibco) with 25 microliters of an Optimem solution containing the plasmid pAAVRSVF9 at a concentration of 0.05 micrograms/microliter (yielding 1.25 µg DNA). The Optimem solution containing the plasmid was preincubated for ½ hour at 37° C. with 1 µg of MBP-Rep 78.

Eighteen hours following the addition of the liposomes, serum containing medium is added to the cells. On the following day the cells are put into solution using standard trypsinization technique and reinfused into the patient using an indwelling portal vein catheter placed at the time of the initial partial hepatectomy. The catheter is removed following the reinfusion of the cells. The hepatic cells reingraft and produce human Factor IX, thereby ameliorating the patient's Factor IX deficiency.

Example 3

In Vivo Treatment of Hemophilia B Using Portal Vein Infusion of Liposomes

Figure 16:
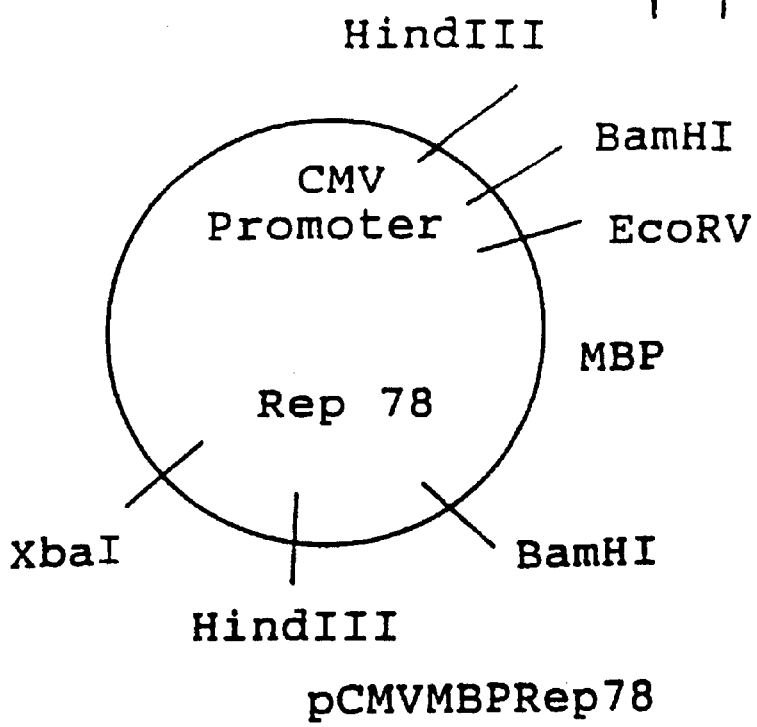
FIG. 16 is a map of plasmid pCMVMBP-rep78.

A lipid that is stable in the presence of serum is used to form liposomes. The liposomes are made by first mixing 5 microliters of the lipid in 25 microliters of a solution appropriate for formation of in vivo liposomes. This lipid solution is then mixed with 25 microliters of a solution containing 1.25 micrograms of the plasmid pAAVRSVF9 and 1 microgram of either MBP-Rep 78 or a plasmid that contains the gene for Rep 78. The solution used is one appropriate to the formation of liposomes that can be used in vivo. pCMVMBPRep78 (FIG. 16) is an example of a plasmid that contains the gene for Rep 78. pCMVMB-PRep78 was constructed as follows:

Using PCR, the ATG sequence located adjacent to the EcoRV site in the 5' untranslated region of pMBP rep 78 was changed to AGT. The oligonucleotides used in this PCR had the sequences:

5'-ATATCAATTCACACAGGAAACG-3' and

5'-GTTCGAATAGATCTTCTATTGG-3'.

The resultant plasmid, pMBPAGTRep78, then was digested with EcoRV and XbaI. The MBP-Rep 78 fragment then was cloned into the plasmid pCDNA, which had been opened with EcoRV and XbaI. The resultant plasmid, pCMVMB-PRep78 (FIG. 16) has the gene for MBP-Rep 78 under the control of the CMV promoter.

If the MBP-Rep 78 protein is used to form the liposome, then the DNA and the protein are preincubated at 37° C. in the Optimem solution for ½ hour prior to mixing with the lipid-Optimem mixture. The liposomes are then delivered to the liver of a patient with Hemophilia B using a portal vein catheter. The catheter is placed on the day of infusion using appropriate coagulation factor support. A rough estimation of the number of hepatocytes that the patient has is made given his/her body mass index, and liposomes diluted in sterile saline are infused such that approximately 1.25 micrograms of DNA are administered per $5 \times 10^5$ hepatocytes. The portal vein catheter is removed and the patient taken for appropriate post-surgical care. Following uptake, those cells stably transduced begin production of human Factor IX, thereby ameliorating the patient's coagulation factor deficiency.

Example 4

In Vivo Treatment of Hemophilia B Using Liposomes and Hepatic-selective Ligands

Liposomes are formed as described in Example 3, except that a hepatic selective ligand, such as asialoglycoprotein, is anchored in the membrane phase of the liposome. The ligand can be incorporated at the time of liposome formation using an appropriate lipid tail connected to the ligand, or the ligand can be incorporated following formation of the liposomes. In the latter case, the ligand can be attached to the membrane using any of a variety of standard techniques, including covalent chemical bond formation between the ligand and a membrane bound protein. The liposomes are administered intravenously in a patient with Hemophilia B. As the liposomes travel through the systemic circulation they are selectively taken up by hepatocytes because the ligand binds to a receptor on the hepatocyte surface. This leads to hepatic-specific uptake and hence expression of the human Factor IX gene, thereby ameliorating the patient's coagulation deficiency.

Example 5

Figure 18:
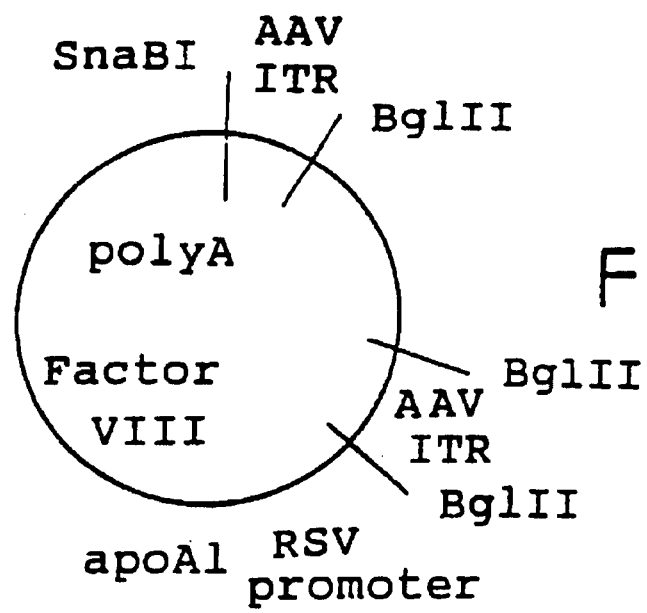
FIG. 18 is a map of pAAVRSVApoF8.
Figure 17:
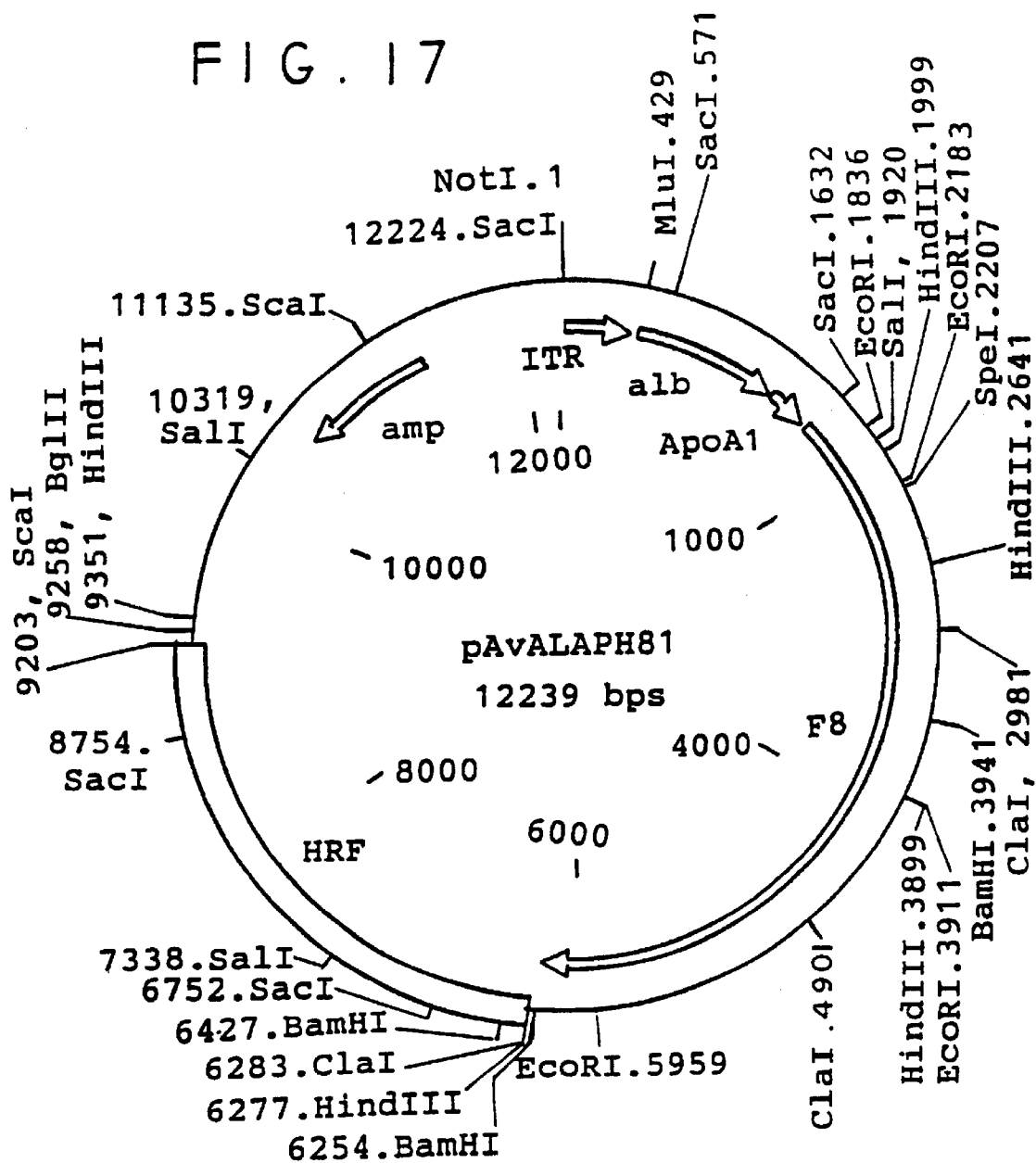
FIG. 17 is a map of plasmid pAvALAPH81.

Ex Vivo Treatment of Hemophilia A Using an AAV Vector for Human Factor VIII and Human Endothelial Cells Reimplanted Using an Osmotic Pump pAvALAPH81 (FIG. 17, which includes an adenoviral 5' ITR, an albumin promoter, and ApoA1 transcription initiation site, a human Factor VIII coding sequence, and an adenovirus homologous recombination fragment) was digested with SalI and ClaI to obtain an ApoAI—Factor VIII fragment. The fragment is blunt-ended with Klenow, and then blunt cloned into pAAVRSVF9. The pAAVRSVF9 plasmid is opened by digestion with EcoRV and ClaI to remove the Factor IX—poly A portion of the plasmid. The remaining fragment contains the AAV ITR's and the RSV promoter. The result of the pAvALPH81 cloning into pAAVRSVF9 is pAAVRSVApoF8 (FIG. 18).

Endothelial cells are isolated from the veins of a patient with Hemophilia A (Factor VIII deficiency) and maintained in culture at 37° C. Liposomes are formed as follows: 1.5 µg of plasmid pAAVRSVApoF8 and 1.2 µg of MBP-Rep 78 are added to Optimem solution (Gibco) to yield a total volume of 25 microliters. This mixture is gently triturated and incubated at 37° C. for ½ hour. Following incubation, the DNA-Rep solution is mixed with a solution that consists of 3 microliters of lipid in 25 microliters of Optimem. The resultant mixture is gently triturated and allowed to sit for ½ hour at room temperature.

The endothelial cells are gently washed with 1X PBS and then gently rewashed two times with Optimem. For every $10^5$ cells, 25 microliters of liposomes are added. The cells are returned to a 37° C. incubator for 12 hours, and then serum-containing medium is added. At 4 weeks following this procedure Factor VIII production by the cells is verified. The cells are put into solution by standard trypsinization followed by inactivation of the trypsin with serum-containing medium. The cells are seeded onto the inner surface of the tubing of an osmotic pump device and the pump is implanted subcutaneously in the forearm of the patient. The cells in the pump produce Human Factor VIII and this protein diffuses from the osmotic pump into surrounding tissues. It is then taken up into the patient's bloodstream, correcting the Factor VIII deficiency.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A composition for delivering a DNA sequence to a cell through integration of said DNA into a chromosome of said cell, wherein said composition does not generate viral particles, and wherein such composition comprises genetic material consisting essentially of:

(a) a first genetic construct for integration into a chromosome of said cell, said first genetic construct being free of DNA encoding adeno-associated virus rep protein and including, in a 5' to 3' direction, a first adeno-associated viral ITR; a promoter controlling a DNA encoding a polypeptide or genetic transcript of interest and a DNA encoding a polypeptide or genetic transcript of interest; and a second adeno-associated viral ITR; and (b) is a second genetic construct that provides, upon expression, an adeno-associated virus rep protein in trans with respect to said first genetic construct, wherein said adeno-associated virus rep protein is the only adeno-associated viral protein expressed by said second genetic construct.

2. The composition of claim 1, wherein said adeno-associated virus rep protein is selected from the group consisting of Rep 78, Rep 68, Rep 52, Rep 40 and fragments or derivatives thereof that retain some or all of the same biological activities as the unmodified Rep 78, Rep 68, Rep 52 or Rep 40.

3. The composition of claim 2, wherein said adeno-associated virus Rep protein is the Rep 78 protein or fragment or derivative thereof that retains some or all of the same biological activities of the unmodified Rep 78 protein.

4. The composition of claim 1, wherein said polypeptide of interest is a therapeutic agent.

5. The composition of claim 1, and further comprising an encapsulating medium.

6. The composition of claim 5, wherein said encapsulating medium is a liposome.

7. The composition of claim 6, wherein said liposome further contains a ligand specific for a desired target cell, tissue, or organ.

8. An isolated eukaryotic cell transfected with the composition of claim 4.

9. A process for transducing a cell in vitro with a DNA sequence, which process comprises contacting said cell with genetic material coding for products that do not generate viral particles, wherein said genetic material consists essentially of:

(a) a first genetic construct for integration into a chromosome of said cell, said first genetic construct being free of DNA encoding adeno-associated virus rep protein and including, in a 5' to 3' direction, a first adeno-associated viral ITR, a promoter controlling a DNA encoding a polypeptide or genetic transcript of interest and a DNA encoding a polypeptide or genetic transcript of interest; and a second adeno-associated viral ITR; and (b) a second genetic construct that provides, upon expression, an adeno-associated virus rep protein in trans with respect to said first genetic construct and wherein said cell is transduced with said first genetic construct and said second genetic construct upon contact of said cell with said first genetic construct and said second genetic construct, wherein said adeno-associated virus rep protein is the only adeno-associated viral protein expressed by said second genetic construct.

10. A composition for delivering a DNA sequence to a cell through integration of said DNA into a chromosome of a cell, wherein said composition does not generate viral particles, and wherein said composition comprises:

(a) genetic material, wherein said genetic material consists essentially of a genetic construct for integration into a chromosome of said cell, said genetic construct being free of DNA encoding adeno-associated virus rep protein and including, in a 5' to 3' direction, a first adeno-associated viral ITR; a promoter controlling a DNA encoding a polypeptide or genetic transcript of interest and a DNA encoding a polypeptide or genetic transcript of interest; and a second adeno-associated viral ITR; and (b) an adeno-associated virus rep protein, said adeno-associated virus rep protein being provided in trans with respect to said genetic construct, wherein said adeno-associated virus rep protein is the only adeno-associated viral protein included in said composition.

11. A process for transducing a cell in vitro with a DNA sequence, which process comprises contacting said cell with (a) genetic material coding for products that do not generate viral particles, wherein said genetic material consists essentially of a genetic construct for integration into a chromosome of a cell, said genetic construct being free of DNA encoding adeno-associated virus rep protein and including, in a 5' to 3' direction, a first adeno-associated viral ITR; a promoter controlling a DNA encoding a polypeptide or genetic transcript of interest and a DNA encoding a polypeptide or genetic transcript of interest; and a second adeno-associated viral ITR; and (b) an adeno-associated virus rep protein provided in trans with respect to said genetic construct, and wherein said cell is transduced with said genetic construct upon contact of said cell with said genetic construct and said rep protein, wherein said rep protein is the only adeno-associated viral protein which is present as a result of said process and which contacts said cell.

12. The composition of claim 10, wherein said adeno-associated virus rep protein is selected from the group consisting of Rep 78, Rep 68, Rep 52, Rep 40 and fragments or derivatives thereof that retain some or all of the same biological activities as the unmodified Rep 78, Rep 68, Rep 52 or Rep 40.

13. The composition of claim 12, wherein said adeno-associated virus Rep protein is the Rep 78 protein or fragment or derivative thereof that retains some or all of the same biological activities of the unmodified Rep 78 protein.

14. The composition of claim 10, wherein said polypeptide of interest is a therapeutic agent.

15. An isolated eukaryotic cell comprising the composition of claim 14.

16. The composition of claim 10, further comprising an encapsulating medium.

17. The composition of claim 16, wherein said encapsulating medium is a liposome.

18. The composition of claim 17, wherein said liposome further contains a ligand specific for a desired target cell, tissue, or organ.

* * * * *